(12) United States Patent
King et al.

(10) Patent No.: US 11,937,919 B2
(45) Date of Patent: Mar. 26, 2024

(54) APPARATUS AND ASSOCIATED ACCESSORIES, METHODS AND USES FOR VISUALISING A PRINT ON AN OBJECT

(71) Applicant: THE SECRETARY OF STATE FOR DEFENCE, Salisbury (GB)

(72) Inventors: Roberto Stefano Pasquale King, Evesham (GB); Martin Wayne Millington, Evesham (GB); Andrew Worsfold, Evesham (GB)

(73) Assignee: The Secretary of State for Defence, Salisbury (GB)

( * ) Notice: Subject to any disclaimer, the term of this patent is extended or adjusted under 35 U.S.C. 154(b) by 221 days.

(21) Appl. No.: 17/250,818

(22) PCT Filed: Sep. 13, 2019

(86) PCT No.: PCT/GB2019/000135
§ 371 (c)(1),
(2) Date: Mar. 5, 2021

(87) PCT Pub. No.: WO2020/053542
PCT Pub. Date: Mar. 19, 2020

(65) Prior Publication Data
US 2021/0393169 A1      Dec. 23, 2021

(30) Foreign Application Priority Data

Sep. 14, 2018    (GB) ...................................... 1815050

(51) Int. Cl.
*A61B 5/1172*    (2016.01)
*B05D 1/00*      (2006.01)
(Continued)

(52) U.S. Cl.
CPC .............. *A61B 5/1172* (2013.01); *B05D 1/60* (2013.01); *C23C 16/4485* (2013.01); *C01B 21/00* (2013.01); *C23C 14/00* (2013.01)

(58) Field of Classification Search
CPC ......... A61B 5/1172; B05D 1/60; C01B 21/00; C23C 14/00; C23C 16/4485
(Continued)

(56) References Cited

U.S. PATENT DOCUMENTS 6,423,946 B1    7/2002  Berka et al.
7,487,739 B1    2/2009  Weaver et al.
(Continued)

FOREIGN PATENT DOCUMENTS

EP    2385790 A1    2/2019
GB    2561712 B     10/2018
(Continued)

OTHER PUBLICATIONS

International Patent Application No. PCT/GB2019/000135, International Preliminary Report on Patentability dated Mar. 25, 2021, 14 pages.
(Continued)

*Primary Examiner* — Jeffrie R Lund
(74) *Attorney, Agent, or Firm* — Kilpatrick Townsend & Stockton LLP (57) ABSTRACT

The invention relates to an apparatus for the visualisation of a print on an object, the apparatus comprising: a base comprising a heating element in thermal communication with a receptacle for storing an agent, a housing to provide a sealed chamber; and a port for applying a vacuum to, or releasing a vacuum from, the sealed chamber. The invention is particularly for the visualisation of a fingerprint such as a latent fingerprint. The invention also relates to a system incorporating the apparatus with a cartridge and agent, and (Continued)

associated methods and uses for visualising a print on an object.

25 Claims, 4 Drawing Sheets

(51) Int. Cl.
*C01B 21/00* (2006.01)
*C23C 14/00* (2006.01)
*C23C 16/448* (2006.01)

(58) Field of Classification Search
USPC ........................................................ 118/31.5
See application file for complete search history.

(56) References Cited

U.S. PATENT DOCUMENTS

| | | |
|---|---|---|
| 8,430,054 B1 | 4/2013 | Hunter et al. |
| 2012/0141669 A1 | 6/2012 | Stones |
| 2021/0393169 A1* | 12/2021 | King .................... A61B 5/1172 |

FOREIGN PATENT DOCUMENTS

| | | | | |
|---|---|---|---|---|
| GB | 2578815 A | * | 5/2020 | ........... A61B 5/1172 |
| GB | 2578815 B | * | 8/2021 | ........... A61B 5/1172 |
| WO | 8801616 A1 | | 3/1988 | |
| WO | 2014142934 A1 | | 9/2014 | |

OTHER PUBLICATIONS

United Kingdom Patent Application No. GB1815050.8, Search Report dated Mar. 11, 2019, 5 pages.
United Kingdom Patent Application No. GB1913087.1, Combined Search and Examination Report dated Mar. 4, 2020, 8 pages.
International Patent Application No. PCT/GB2019/000135, International Search Report and Written Opinion dated Nov. 22, 2019, 18 pages.
Thewalt, et al., "$S_4N_4$ and its Derivatives: Preparation, Structure and Thermolysis of CuBr $S_4N_4$," Zeitschrift fur Naturforschung—Section B Journal of Chemical Sciences, Jul. 1, 1982, pp. 828-831, vol. 37, No. 7.
Bleay, et al., "Polymerisation $S_2N_2$ to $(SN)_x$ as a tool for the rapid imaging of fingerprints removed from metal surfaces," Journal of Materials Chemistry, Oct. 15, 2010, pp. 10100-10102, vol. 20, No. 45, The Royal Society of Chemistry.
Kelly, et al., "Fingerprint and Inkjet-Trace Imaging Using Disulfur Dinitride," Chemical Communications, Oct. 17, 2008, The Royal Society of Chemistry.

* cited by examiner

APPARATUS AND ASSOCIATED ACCESSORIES, METHODS AND USES FOR VISUALISING A PRINT ON AN OBJECT

TECHNICAL FIELD OF THE INVENTION

The invention relates to an apparatus for the visualisation of a print on an object, particularly a fingerprint such as a latent fingerprint. The invention also relates to a system, and associated methods and uses, in particular for generating disulfur dinitride ($S_2N_2$) from the metal halide adduct of tetrasulfur tetranitride ($S_4N_4$) for visualising a print on an object.

BACKGROUND TO THE INVENTION

The use of prints in solving crimes is still of high importance. Since the late nineteenth century, fingerprint identification methods have been used by police agencies around the world to identify suspected criminals. The basis of the traditional fingerprinting technique is based on the observation that the skin on the palmar surface of the hands and feet forms ridges, so-called papillary ridges, in patterns that are unique to each individual and which do not change over time.

There are three different types of fingerprints: visible, impression, and latent. Visible prints are also called patent prints and are left in some medium, like blood or ink that reveals them to the naked eye. They can occur, for example, when blood, dirt, ink or grease on a finger come into contact with a smooth surface of an object and leave a friction ridge impression that is visible without development. Impression prints are also called plastic prints and are indentations left in soft pliable material, for example clay, wax and paint, which will take the impression. They are visible and often can be viewed or photographed without development. Latent prints are not apparent to the naked eye. They are formed from the sweat from sebaceous glands on the body or water, salt, amino acids and oils contained in sweat. The sweat and fluids create prints that must be developed before they can be seen or photographed.

Investigators normally need a portable, permanent copy of the fingerprints. A photograph can generally fulfil this need. Of the three types of fingerprints, visible fingerprints can be photographed directly, and impression fingerprints can usually be photographed under special lighting conditions, but invisible latent fingerprints are difficult to photograph. They must first be made visible.

Ways to render latent fingerprints visible, so that it is possible to photograph such prints, can be complex and may depend, for example, on the type of objects on which they have been left. It is generally necessary to use a 'developer', usually a powder or chemical reagent, to produce a high degree of visual contrast between the ridge patterns and the object on which a fingerprint has been deposited.

Developing agents often depend on the presence of organic materials or inorganic salts for their effectiveness, although the water deposited may also take a key role. Fingerprints are typically formed from the aqueous-based secretions of the eccrine glands of the fingers and palms with additional material from sebaceous glands primarily from the forehead. This latter contamination results from the common human behaviors of touching the face and hair.

Examples of techniques which use developing agents include techniques using ninhydrin or diazafluorenone, vacuum metal deposition and ethyl cyanoacrylate polymerisation. Other methods, such as the application of fine powders, work by adhesion to sebaceous deposits and possibly aqueous deposits in the case of fresh fingerprints. However, physical removal of the fingerprint deposit itself therefore renders many, if not all, conventional techniques inadequate. Examples of such situations are when the prints have been removed deliberately to avoid detections, where the prints have been removed through the effects of percussion/explosion or where the object comprising the print has been submersed in a liquid, such as water.

It has been observed that $S_2N_2$ vapour is a suitable development agent for latent fingerprints (Kelly et al. 2008. Fingerprint and inkjet-trace imaging using disulfur dinitride. Chem. Commun. 6111-6113). Traditional generation of $S_2N_2$ has been achieved via thermal pyrolysis of purified $S_4N_4$ through silver wool. Although purified $S_4N_4$ has previously be shown to be an effective precursor molecule for yielding a high purity of $S_2N_2$ for fingerprint visualisation purposes, $S_4N_4$ is friction-sensitive and carries a risk of explosion if not handled correctly.

Recent advances as described in GB1804040.2 have identified a safer means of generating $S_2N_2$, from the metal halide adduct of $S_4N_4$, for the purpose of visualising a print on an object. Furthermore, the $S_2N_2$ produced by the method of GB1804040.2 has been shown to be highly adept at recovering different types of prints from a variety of materials and objects, in particular materials and objects that have been tampered with or undergone a force or treatment that may have rendered the print more difficult to recover or visualise with other visualisation techniques. However, a problem with the use of $S_2N_2$ vapour is its tendency to leave a staining residue on the surface of the apparatus in which the vapour is generated, which leaves the apparatus in an undesirable state, as well as making it difficult to visualise an object in the apparatus to assess any progress in terms of print development.

Thus, there is a need for an apparatus which provides for the controlled generation of $S_2N_2$ vapour in a manner that reduces or eliminates such staining.

SUMMARY OF THE INVENTION

According to a first aspect, the invention provides an apparatus for visualising a print on an object, the apparatus comprising: a base defining a surface, the base comprising a first heating element for heating an agent to generate a vapour for developing a print on the object, the first heating element in thermal communication with a receptacle for receiving the agent to be heated, the receptacle protruding from the surface of the base; a housing for contacting with the base to provide a sealed chamber for enclosing the object; and a port for applying a vacuum to or releasing a vacuum from the sealed chamber.

The term 'print' for the purpose of the invention may be a fingerprint, ear print, lip print, palm print, foot print, ink print or shoe print. Preferably, the print is a fingerprint. As used herein, the term fingerprint encompasses thumb prints.

The term 'object' for the purpose of the invention may be any object which may comprise a print to be visualised, such as a print on the surface of the object, and can be of any material on which a print can be retained. Examples of materials which may contain a print to be visualised include but are not limited to metal, paper, cardboard, wood, fabric, plastic, glass or a combination thereof. Suitable metals include but are not limited to iron, steel, brass, bronze, zinc, gold, silver, platinum, tin, copper, lead, nickel, chromium, titanium and aluminium and mixtures and alloys thereof.

Suitable fabrics include but are not limited to cotton, linen, polyester, nylon and other man-made fabrics and mixtures thereof.

The term 'agent' for the purpose of the invention refers to any agent capable of developing a print on an object. It is understood that envisaged agents for this particular apparatus includes metal halides of $S_4N_4$, preferably $CuBr.S_4N_4$, capable of generating $S_2N_2$ vapour upon heating. However, it is to be appreciated that other agents could be used in the apparatus, particularly those agents which are required to undergo heating in order to generate a vapour capable of visualising a print on an object.

In one embodiment, the receptacle is designed to receive an agent. The receptacle is also designed such that any agent vapour generated as a result of heating the receptacle, containing agent, permeates into the sealed chamber.

The relative dimensions of the receptacle, most likely in combination with only a portion of the receptacle being in contact with, or being directly heated by, the first heating means, may in particular contribute to the arrangement being capable of generating a cleaner (reducing staining) environment for visualising a print. This may be achieved in a number of ways, as follows.

The arrangement of the protruding receptacle in the apparatus may allow a thermal gradient to be generated in the receptacle upon heating by the first heating element, which enables polymerising residue, given off by the agent as a result of heating, to be collected on an interior surface of the receptacle, such as at cooler regions of the receptacle as a result of the thermal gradient, rather than collecting on other surfaces within the sealed chamber, for example on the interior housing surface or the surface of the base, while still allowing for vapour to contact the object and develop any print(s) on the object surface. For example, the receptacle may comprise a first portion, at the base of the receptacle, in contact with, or designed to be heated directly by, the first heating means, with a second portion, adjacent to the opening to the receptacle, either not in contact with, or not directly heated by, the first heating means. The thermal gradient may be enabled by the first portion of the receptacle, at the base, being comprised of, or consisting essentially of a good conductor of heat, such as a metal (in one embodiment the metal is aluminium), whilst the second portion comprises, or consists essentially of, a poor conductor of heat, or even an insulating material, such as glass. The heat conducted within the first portion would thus dissipate (become cooler) increasingly through the second portion, towards the opening of the receptacle, providing the thermal gradient.

Thus, preferably, the protruding receptacle is arranged such that the first heating element is capable of generating a thermal gradient in the receptacle.

The protruding receptacle may be arranged substantially perpendicular to the base. Thus, preferably the protruding receptacle is arranged substantially perpendicular to the base such that the first heating element is capable of generating a thermal gradient.

In addition, or alternatively, the receptacle may provide for funneling which enables collection of polymerising residue on the interior surface of the receptacle, while still allowing for vapour to contact the object and develop any print(s) on the object surface The first portion of the receptacle may be of similar dimensions to that of the second portion, such as being of equal height (or length), however the second portion may alternatively be approximately half, twice or three times the height of the first portion. In one embodiment the second portion is approximately 1.5 times the height of the first portion. In one embodiment, the height of the first portion may be approximately 20 mm, whereas the height of the second portion may be approximately 30 mm.

Thus, in use an agent may be added directly to the protruding receptacle of the apparatus, with the first heating element being used to provide a thermal gradient within the receptacle, and/or the receptacle providing for funneling of the agent vapour, such that polymerising residue, generated from the agent as a result of heating, being collected directly on the interior surface of the receptacle, rather than collecting on other surfaces within the sealed chamber.

In one embodiment of the apparatus of the first aspect, the receptacle is designed to receive a cartridge containing the agent, wherein the cartridge is preferably of dimensions, and in use is arranged with respect to the first heating element and the receptacle, such that the thermal gradient, and/or the funneling, is generated in the cartridge, either instead of or in addition to the receptacle.

Thus, according to a second aspect, the present invention provides a system for visualising a print on an object, the system comprising: the apparatus of the first aspect; a cartridge designed to be, or suitable for being, inserted into the receptacle of the first aspect; and an amount of agent within the cartridge, wherein the agent is a metal halide of $S_4N_4$.

The size and/or shape (dimensions) of the cartridge are preferably such that the thermal gradient, and/or the funneling, is generated in the cartridge, either instead of or in addition to the receptacle. The thermal gradient may be achieved by the cartridge being longer (or higher) than the height of the receptacle, such that a portion of the cartridge protrudes from the top of the receptacle, or may be through only a portion of the cartridge being capable of being contacted with, or being directly heated by, the first heating means. The thermal gradient may also, at least in part, be provided by the receptacle being comprised, or consisting essentially of, a good conductor of heat, such as a metal (for example aluminium), and the cartridge being comprised, at least in part, of a poor conductor of heat, or an insulator, such as glass.

Preferably the cartridge has a height (or length) of at least 1.5 times the depth of the receptacle. For example, if the receptacle has a depth of approximately 20 millimetres, a suitable cartridge would preferably have a height of at least approximately 30 millimetres (i.e. in use, two thirds of the cartridge would be held within the receptacle while one third of the cartridge protrudes from the receptacle). Further preferably, the cartridge has a height of at least 2 times the depth of the receptacle. For example, if the receptacle has a depth of approximately 20 millimetres, a suitable cartridge would have a height of approximately 40 millimetres (i.e. in use, one half of the cartridge is held within the receptacle, with the other half of the cartridge protruding from the receptacle). Further preferably still, the cartridge has a height of at least 2.5 times the depth of the receptacle. For example, if the receptacle has a depth of approximately 20 millimetres, a suitable cartridge would have a height of approximately 50 millimetres (i.e. in use, two-fifths of the cartridge is held within the receptacle while three-fifths of the cartridge protrudes from the receptacle). Altering the relative dimensions, and/or materials, of the receptacle and/or cartridge provides for optimisation of the thermal gradient, and/or the funneling, generated in the receptacle and/or cartridge, which in turn optimises the capture and control of residue, given off by the agent as a result of heating, contributing to a cleaner environment for visualising prints.

The cartridge preferably comprises a sealable means designed to be removed prior to use, such as a screw cap or other such means.

The cartridge contains an amount of agent, preferably a pre-measured or pre-weighed amount of agent.

Thus, it is envisaged in a preferred embodiment that the cartridge contains a pre-measured or pre-weighed amount of agent sealed within the cartridge, and that the sealable means is removed prior to use of the system.

The agent is a metal halide of $S_4N_4$. Preferably, the agent is $CuBr.S_4N_4$.

The inclusion of a metal halide adduct of $S_4N_4$, preferably $CuBr.S_4N_4$, as a precursor material to $S_2N_2$ vapour, allows for the efficiency and safety of the print visualisation technique to be increased. Such use optionally facilitates operational flexibility as the amount of precursor used per run may be varied (particularly increased) based on both the substrates type and treatment chamber size, without increasing the safety risk to a user, such as a forensic scientist, or indeed to the equipment, especially from risk of explosion.

Using the metal halide adduct of $S_4N_4$, in particular generated from $S_4N_4$ obtained without prior purification, provides for producing $S_2N_2$ vapour which is superior at developing fingerprints on certain materials, in particular metal objects, when compared to more conventional methods such as cyanoacrylate fuming. For example, DNA is unaffected by $S_2N_2$ treatment produced, which is clearly an attractive feature from a crime scene evidence collection perspective. Furthermore, $S_2N_2$ vapour is particularly suitable for visualising prints that are not readily visible to the naked eye, such as latent prints. The method can be used to improve the visibility of a print that is at least in part visible to the naked eye. $S_2N_2$ produced from $S_4N_4$ obtained without prior purification, is highly adept at recovering different types of prints from a variety of materials and objects, in particular materials and objects that have been tampered with or undergone a force or treatment that may have rendered the print more difficult to recover or visualise with other visualisation techniques. It has been found that $S_2N_2$ can be used to visualise prints on surfaces that have been subjected to wetting, heat and/or friction. For example, $S_2N_2$ can still be successful even if the object has been cleaned, submersed in water or been subjected to percussion and/or explosion. The object comprising the print may be a used gun cartridge that has been subjected to the force and heat of firing the gun. $S_2N_2$ can also be used to visualise prints on objects that have been deliberately washed, for example by cleaning with a detergent. $S_2N_2$ generated from $S_4N_4$ is particularly suitable for visualising prints on a metal surface, such as brass or stainless steel, which has been cleaned or washed.

The apparatus of the first aspect, either by itself or as part of the system of the second aspect of the present invention, has been shown to provide the primary advantage of a cleaner (reduced staining) environment for visualising a print. The apparatus also enables prints to be developed more efficiently. For previous apparatus designed for use of the metal halide of $S_4N_4$, such as $CuBr.S_4N_4$, considerable staining was observed on the interior surface of its chamber as a result of $S_2N_2$ vapour polymerising on this surface (in addition to polymerising on the object to visualise a print). Typically, a dark blue/black polymer forms during the use of $S_2N_2$, although under certain conditions the polymer may appear to be gold in colour. The Inventors have found that the protruding receptacle of the apparatus of the first aspect, either by itself or in combination with the cartridge in the system of the second aspect, in thermal communication with the first heating element, enables polymerising residue, given off by the agent as a result of heating, to be collected on the interior surface of the receptacle, or where applicable the cartridge, rather than collecting on other surfaces within the sealed chamber, for example on the interior housing surface or the surface of the base. Thus, in the context of the use of $S_2N_2$ vapour for visualising a print in the apparatus of the invention, polymer by-products are primarily observed on the interior surface of the receptacle, or cartridge, for example as a black-coloured ladder forming up the side surface, rather than dispersed onto other areas of the apparatus. As a result, a cleaner environment is provided for prints to be developed, and the progress of such visualisation reactions can be more easily monitored by a user.

The Applicant has found that generation of a thermal gradient and/or the funneling of the agent vapour in the receptacle, or as applicable the cartridge, is capable of removing undesirable $S_2N_2$ polymerisation products upon the heating of the $S_4N_4$, or metal halide adducts thereof. The thermal gradient is achieved for example where the receptacle, or cartridge, is hotter at its base, where the $S_4N_4$ agent is placed prior to heating, relative to the top and/or upper region of the receptacle, or cartridge, where the vapour is released into the sealed chamber upon generation. Thus, for example, in the case of $S_2N_2$ generation, the first heating element and receptacle arrangement, either by itself of in combination with the cartridge, ensures that any $S_2N_2$ polymerisation, as a result of cooling when passing up the receptacle, or as applicable the cartridge, with the thermal gradient, is deposited at the cooler region of the receptacle, or as applicable the cartridge, rather than other locations within the apparatus.

Providing a port in the apparatus of the first aspect, in particular for applying a vacuum to the sealed chamber, mitigates against aerial hydrolysis of the agent and increases vapour pressure. For example, in the case of $S_2N_2$, this allows the $S_2N_2$ vapour to enter the vapour state and diffuse, ultimately helping to induce polymerisation. The apparatus is suitable for containing a vacuum (either a dynamic vacuum or a static vacuum).

An example of a lab scale apparatus may comprise a sealed chamber of up to 10 litres, or alternatively from about 10 to about 50 litres, for example 20 litres. It will be appreciated that the apparatus must be able to maintain the vacuum for a desired period of time, for example in order to implement a method for visualising a print on a surface.

Preferably the apparatus is a portable apparatus, for example a portable apparatus weighing 18 kg to 26 kg.

Preferably, the housing of the apparatus is formed from transparent material. Examples of such material include glass- and/or plastic-based material. This provides the advantage of a viewing window, to aid viewing of the agent, or to monitor the progress in terms of a visible print being developed on the object during use of the apparatus.

Preferably, the housing is connected to the base by a moveable arm. This provides the advantage of ensuring accurate placement of the housing on the surface of the base to provide a sealed chamber. A moveable arm may also provide for automated sealing of the chamber housing A sealing material or means could also be provided on the base and/or the edge of housing to (further) ensure an airtight seal is formed between the housing and the base surface.

Preferably, the first heating element and receptacle are arranged substantially centrally on the base of the apparatus. This provides for a greater uniformity in the sealed chamber in terms of dispersal of agent vapour, ensuring a more consistent contact between the vapour and object.

Preferably, the port is located on the base. This arrangement ensures that the further elements required to provide for a vacuum (for example a vacuum pump, air filter) can be located within the apparatus base beneath the surface of the base, assisting from a design and manufacturing perspective.

Preferably, a cover element is provided to secure the receptacle to the base of the apparatus. This cover element provides advantages including, from a manufacturing perspective, facilitating the protruding receptacle being non-integral relative to the base, i.e. a detachable receptacle. For example, the cover element may fit over the receptacle and be secured to the base via a screw and thread arrangement, thus trapping the receptacle between the base and cover. The cover element is envisaged to have an aperture, aligned with the aperture of the receptacle, through which agent vapour can pass into the sealed chamber during use. Additionally, the cover element may contribute to the thermal gradient generated by the first heating element in the receptacle, for example as a result of the cover element also being in thermal communication with the first heating element. The cover element may also contribute to the receptacle providing for funneling of the agent vapour.

Preferably, the base comprises a second heating element in thermal communication with the surface of the base. This feature provides the advantage of contributing to the quantity and uniformity of agent vapour in the sealed chamber by ensuring that agent vapour does not cool (i.e. as a result of loss of thermal energy), for example when contacting the surface of the base. Preventing crystallisation of $S_2N_2$ on the surface of the base ensures no unwanted loss of agent vapour, and contributes to the apparatus and visualisation being more efficient.

Preferably, the heating element(s) comprise a heater comprising a heating component, a heating sensor and a thermal cut-out. For example, the heater is a cartridge heater or ceramic heater (e.g. a high accuracy platinum resistance (PT100) sensor). This ensures an easily controllable and safe heater is provided in the apparatus i.e. wherein the heating element(s) are capable of quickly reaching the required temperature with minimal overshoot, and for this temperature to be maintained accurately. Preferably, the heating element is processor controlled to ensure a high degree of control accuracy.

Preferably, the apparatus comprises a control interface. Thus, to assist with simplicity of use, the apparatus may be fully processor controllable by a man-machine interface, for example with pre-set steps defining the operation of the apparatus.

According to a third aspect, the invention provides a method for visualising a print on an object using the apparatus of the first aspect, the method comprising the steps of: a) placing the agent in the receptacle; b) arranging the object on or proximal to the base; c) placing the housing on the surface of the base to form a sealed chamber enclosing the object and agent; d) removing air from the sealed chamber via the port to provide a vacuum; e) heating the agent in the receptacle via the first heating element to generate vapour within the sealed chamber; f) allowing the vapour to contact the object; g) releasing the vacuum via the port; h) removing the housing to allow for off-gassing; and i) removing the object for inspection and/or downstream image recording.

According to a fourth aspect, the invention provides a method for visualising a print on an object using the system of the second aspect, the method comprising the steps of: a) placing the cartridge containing the agent in the receptacle; b) arranging the object on or proximal to the base; c) placing the housing on the surface of the base to form a sealed chamber enclosing the object, cartridge and agent; d) removing air from the sealed chamber via the port to provide a vacuum; e) heating the agent in the cartridge via the first heating element to generate vapour within the sealed chamber; f) allowing the vapour to contact the object; g) releasing the vacuum via the port; h) removing the housing to allow for off-gassing; and i) removing the object for inspection and/or downstream image recording.

However, variations to method step a) could be undertaken if necessary e.g. the agent being added to the cartridge when the cartridge is already placed in the receptacle.

Thus, the invention claims the apparatus of the first aspect when used to implement the method of the third aspect, and claims the system of the second to aspect when used to implement the method of the fourth aspect, for visualising a print on an object.

The methods of the invention can be used to visualise a print on a variety of articles. Such articles include but are not limited to: weapons such as a gun, gun cartridge, ammunition, bullet, shell, knife, sword, bayonet, machete; parts of a building such as a window, door or lock; a vehicle; an article of furniture; a tool such as a hammer, screwdriver or crowbar; jewellery; electrical devices; electronic devices; a lock or key; bank notes; and a household article such as a kitchen knife.

Preferably, the agent is a metal halide of $S_4N_4$. Further preferably, the agent is $CuBr.S_4N_4$.

Preferably, the agent is provided in the cartridge of the second aspect.

Preferably, the vacuum is at a pressure of from about $1.33 \times 10^{-6}$ Pa ($1 \times 10^{-9}$ mm/Hg) to about 133 Pa (1 mmHg).

For the sub-atmospheric pressure under vacuum, such as at a pressure of from about $1.33 \times 10^{-6}$ Pa ($1 \times 10^{-9}$ mm/Hg) to about 133 Pa (1 mmHg), this vacuum may be static or dynamic.

A vacuum is obtained using approaches known to the skilled person, for example using a vacuum pump to provide a vacuum within a sealed environment. Once a vacuum has been established, the means by which the vacuum was obtained can optionally be switched off so that the chamber remains under static vacuum. For example, the vacuum pump may be operating up to, or while, the agent (such as the metal halide adduct of $S_4N_4$) is being heated. The vacuum may then be turned off and the vacuum maintained (as a static vacuum) during the agent vapour (e.g. $S_2N_2$ vapour) contacting the object. Alternatively, a dynamic vacuum may be applied during heating of the metal halide adduct. For example, a dynamic vacuum may aid sublimation of the metal halide adduct as well as increasing the vapour pressure of the generated $S_2N_2$.

In the case of the metal halide adduct of $S_4N_4$, heating this agent causes decomposition of the adduct, releasing $S_2N_2$ vapour. Once in the gaseous state the $S_2N_2$ has a high thermal energy. The heating temperature is selected so as to generate $S_2N_2$ vapour, but ideally the heating temperature is controlled to prevent the $S_2N_2$ vapour having excess thermal energy and to prevent/minimise the formation of undesirable by-products.

The temperature required must be sufficient to cause the adduct to decompose and release $S_2N_2$ vapour when heated and will depend on the metal used. Typically the temperature at which the metal halide adduct of $S_4N_4$ is heated is from about 100° C. to about 200° C., for example from about 155° C. to about 190° C., preferably 155° C. to about 180° C., and further preferably about 160° C. These temperatures are particularly suitable when $CuBr.S_4N_4$ is used.

Heating the metal halide adduct of $S_4N_4$ at up to 180° C. for approximately 30 seconds (e.g. 1 minute) can efficiently generate $S_2N_2$. However, longer times are envisaged, for example 5 to 15 minutes, 15 to 30 minutes, 30 to 60 minutes, or 1 to 3 hours. Prolonged heating, intending to generate all the $S_2N_2$ from the metal halide adduct of $S_4N_4$ has not been shown to provide any significant benefits over, for example, a 30 minute heating phase. Although the heater can stay on thorough the time a sealed chamber is formed, is it not necessary. However, maintaining heat helps ensure $S_2N_2$ vapour does not cool as solid $S_2N_2$.

Preferably, for step e) the agent is heated at a temperature of from about 160° C. to 200° C. for at least 30 seconds.

The amount of the metal adduct of $S_4N_4$ to be heated depends on the size of the sample and also on the size of the apparatus in which the method of the invention is conducted. A suitable amount of the metal adduct may be from about 0.1 g to about 5 g, preferably about 0.1 g to about 1 g, and further preferably about 0.1 g to about 0.3 g.

Following (or indeed during) the heating step e), the object comprising a print is contacted with the agent vapour (e.g. $S_2N_2$ vapour) for a sufficient time to visualise the print, for example at least 1 minute, or at least 15 minutes, for example approximately 5 minutes, 15 minutes, 1 hour, or 2 hours, or alternatively overnight, such as for from about 8 hours to about 12 hours. During the contact time, the $S_2N_2$ vapour polymerises on the surface of the object comprising the print. Polymerisation of the $S_2N_2$ results in the visualisation of the print. Typically, a dark blue/black polymer forms only where the print has contacted the surface. Under certain lighting angles the polymer may appear to be gold in colour.

Preferably, for step f) the vapour contacts the object for at least 1 minute.

Preferably, apparatus comprising a second heating element is used, wherein the second heating element heats the surface of the base for a period of time during at least one of steps d) to h) and/or prior to step d). For example, the second heating element can heat the surface of the base at the same time the first heating element is in operation. The second heating element can heat the surface prior to and/or during the vacuum stage to dry any moisture in the chamber, and to assist with the vacuum forming within the sealed chamber.

Preferably, the second heating element is heated at a temperature of from about 25° C. to 160° C. i.e. a temperature typically greater than ambient temperature. Further preferably the second heating element is heated at about 50° C.

Preferably, the apparatus is operated within a fume hood.

Optionally, when undertaking the method of the second aspect of the invention, sample objects can be fixed or held in place within the apparatus of the first aspect (i.e. either on the base or in other location within the sealed chamber) using appropriate means. Suitable means include but are not limited to double-sided tape, Velcro, clipped fastenings or other device or structure for holding the object. This arrangement allows the object to be located at or proximal to a source of a developing agent, for example $S_2N_2$ vapour, to assist in exposure of the object to the developing agent.

Preferably, apparatus comprising a control interface is used, wherein at least one of steps c) to e) and steps g) to h) is controlled by the control interface.

Any suitable recording techniques may be used to preserve information obtained from a visualised print. Thus, the method may also include the step of recording an image of the visualised print, for example by photography.

It is also envisaged that the visualised print can be further enhanced by viewing under polarized light or by the use of sources of light within a particular frequency range such as ultra-violet light or infra-red light by the application of digital imaging processing.

Once visualised, the print can be analysed, for example by comparing the visualised print to another print, such as a print obtained from an alternative source or a print from a record or library.

According to a fifth aspect, the invention provides for use of the apparatus of the first aspect or the system of the second aspect to visualise a print on an object.

Any feature in one aspect of the invention may be applied to any other aspects of the invention, in any appropriate combination. In particular, the apparatus aspects may be applied to system, method and/or use aspects and vice versa. The apparatus, system, method and uses of the invention extends to an apparatus, system, method and uses substantially as herein described, with reference to the Examples.

In all aspects, the invention may comprise, consist essentially of, or consist of any feature or combination of features, including the cartridge described in the system of the second aspect.

The invention will now be described, with reference to the following non-limiting examples and Figures in which:

DETAILED DESCRIPTION

Figure 1:
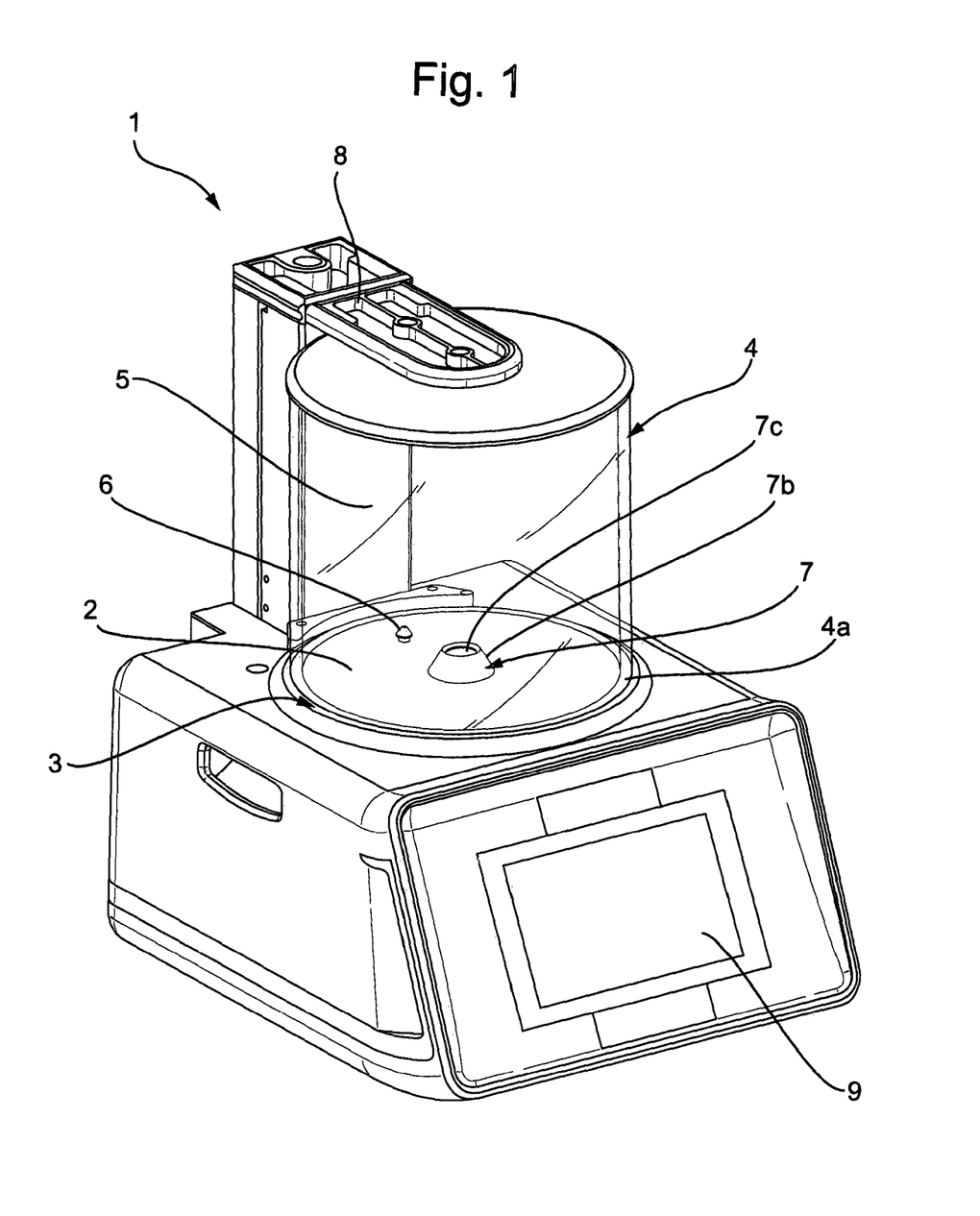
FIG. 1 shows a side perspective view of a laboratory scale apparatus of the invention.
Figure 2:
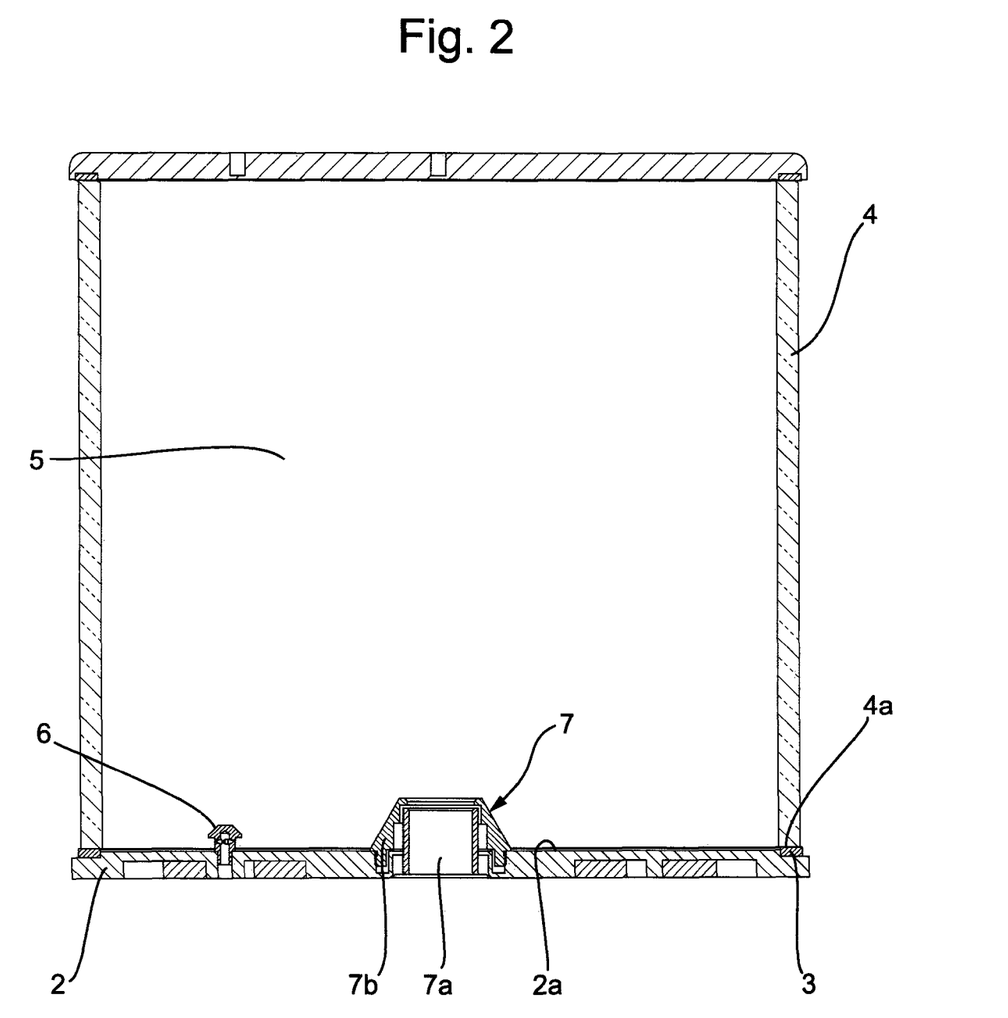
FIG. 2 shows a side sectional view of the chamber and base of the apparatus.

As shown in FIG. 1 and FIG. 2, apparatus (1) comprises a circular base (2) made of stainless steel and providing a surface (2a), surrounded by a circular perimeter (3), and a transparent circular housing (4) made from glass and defining a housing edge (4a). The housing (4) has dimensions of approximately 201 millimetres in diameter by 200 mm millimetres in height and is shown placed on the perimeter section (3) to form a 6.5 litre-volume sealed chamber (5). The perimeter section (3) is made from rubber to assisting in forming an air-tight seal between the perimeter section (3) and the housing edge (4a). An object (not shown) comprising a print can be arranged on or proximal to the base (2) (for example on an object holder (not shown)) such that when the moveable housing (4) is arranged on the surface (2a), the object is enclosed within a sealed chamber. A vacuum port (6) is provided on the base (2) for applying a vacuum to or releasing a vacuum from the sealed chamber (5). In the centre of the base (2) is shown a protruding receptacle (7) formed by a heater pot (7a) (not shown) underneath a cover element (7b). The receptacle (7) has an opening (7c) capable of receiving a glass cartridge (not shown) containing $CuBr.S_4N_4$.

Housing (4) is attached to the apparatus via moveable arm (8) to enable movement of the housing (4) from an open position to a closed position, the latter arrangement provides the sealed chamber (5). Operation of the apparatus, including the controlling the movement of the arm (8) and setting/initiating the programme settings when undertaking a method for visualising a print on an object, is achieved via user control interface (9) which is connected to a processor (not shown) located internally within the apparatus (1).

Figure 3:
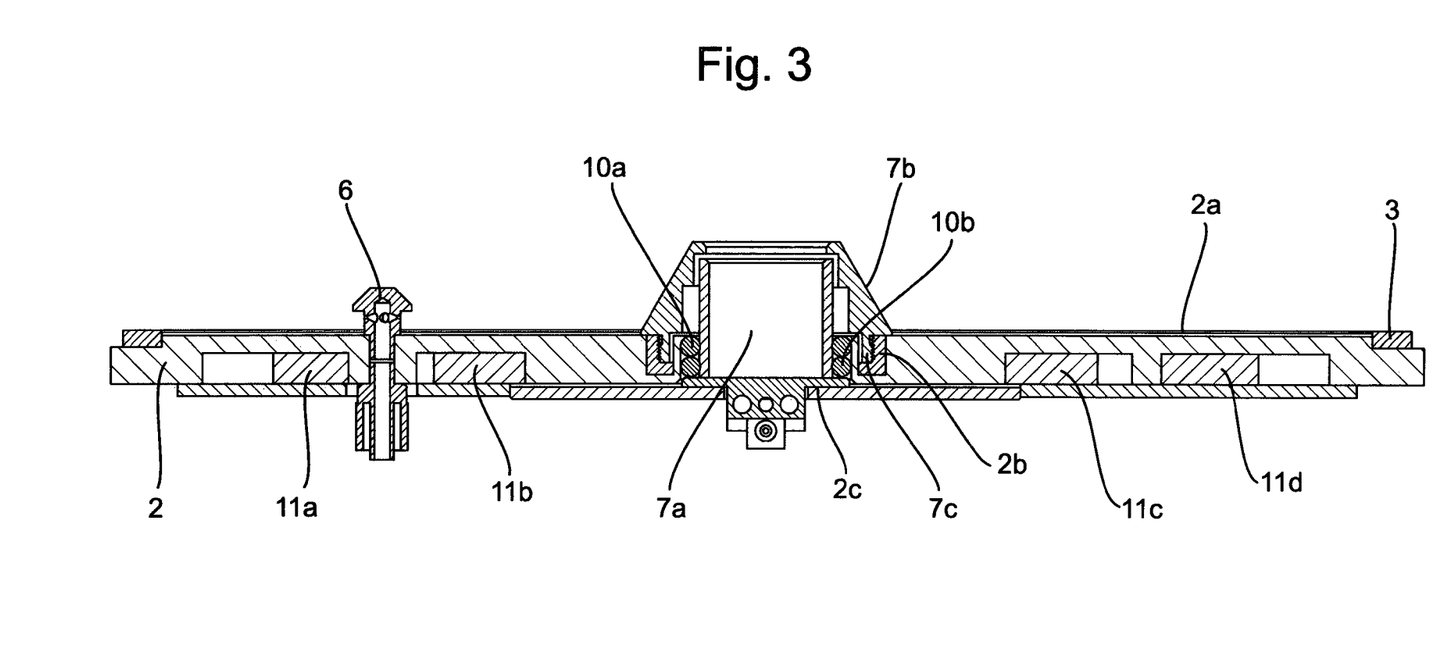
FIG. 3 shows a side sectional view of the base of the apparatus.

As shown in more detail in FIG. 3, the cover element (7*b*) attaches to the base (2) via an extended screw region (7*c*) which is alignable with a thread groove (2*b*). This arrangement ensures the heater pot (7*a*) is securely attached to the base (2) and in thermal communication with a first heating element (10*a*, 10*b*). The arrangement of the first heating element (10*a*, 10*b*) and receptacle (7), when used in combination with a glass cartridge (not shown), ensures a thermal gradient is provided in the cartridge during heating i.e. the cartridge would be hotter at its base and/or lower region (primarily where it contacts the heater pot (7*a*)), relative to the top and/or upper region of the cartridge. Heater pot (7*a*) sits in an indented region of (2*c*) of the base (2) to ensure closer orientation between the first heating element (10*a*, 10*b*) and lower region of the cartridge (not shown) when positioned in the heater pot (7*a*) during use. The cartridge may also provide for funneling of the agent vapour.

Figure 4:
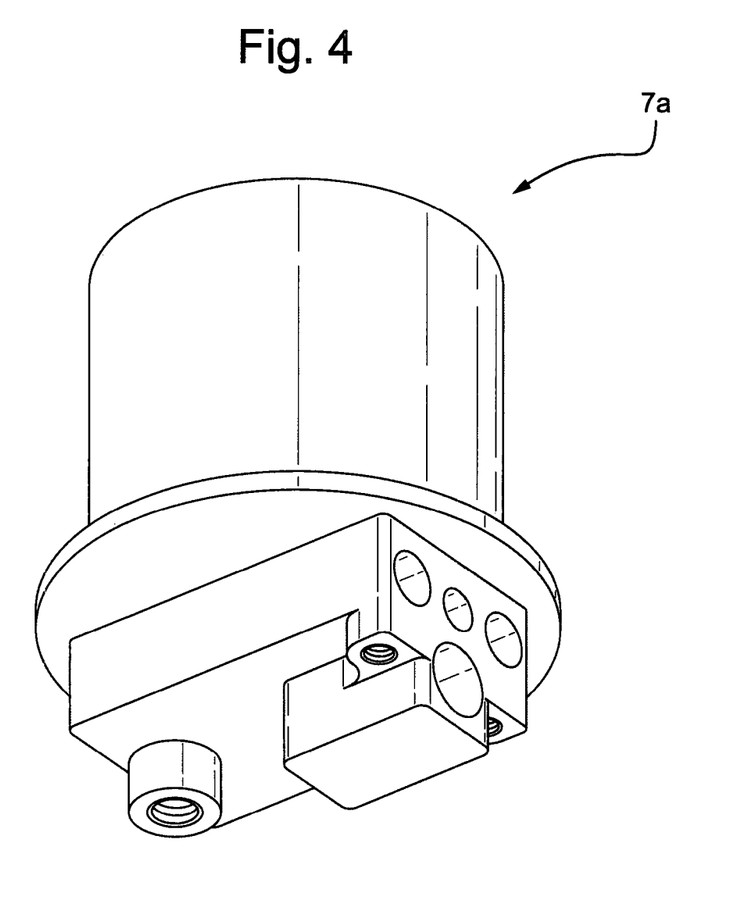
FIG. 4 shows a side perspective view of a heater pot of the apparatus.

Shown in FIG. 4 is a heater pot (7*a*) made of aluminium and comprising a silver anodise finish. The heater pot (7*a*) is 20 millimetres in diameter (19 millimetres in internal diameter to provide for tolerance of the cartridge) and 28.5 millimetres in height. The heater pot (7*a*) has an opening of 20 millimetres in depth for receiving the cartridge (not shown) of 17 millimetres internal diameter by 50 millimetres in height and containing $CuBr.S_4N_4$. This arrangement ensures that, in use, the lower region of the cartridge of depth of 20 millimetres, including the $CuBr.S_4N_4$ collected on the base of the cartridge, sits within the heater pot (7*a*), ensuring a direct thermal communication between first heating element (10*a*, 10*b*) and the lower region (including the base) of the cartridge due to thermal conduction and radiated heat. The upper region of the cartridge (i.e. approximately 30 millimetres in height) lies outside the receptacle (7) in use. Thus, the arrangement of the cartridge in the receptacle (7) (primarily the heater pot (7*a*)) ensures a thermal gradient, and/or funneling, is provided across the cartridge such that unwanted $S_2N_2$ polymerisation is captured on the inner sides of the cartridge.

Located in a region of the base (2) between the protruding receptacle (7) and the circular perimeter (3) is an arrangement of a second heating element (11*a*, 11*b*, 11*c*, 11*d*) in thermal communication with the base surface (2*a*). The second heating element (11*a*, 11*b*, 11*c*, 1*d*) contributes to the quantity and uniformity of $S_2N_2$ vapour in the sealed chamber by ensuring that agent vapour does not cool on the surface (2*a*) of the base (2).

In use, apparatus (1) is operated in a fume hood and programmed/operated using the control interface (9). A cartridge containing $CuBr.S_4N_4$ is placed in receptacle (7) of apparatus (1) to provide a system for visualising a print on an object. The seal is removed from the cartridge to enable $S_2N_2$ vapour to be released into the sealed chamber when the system is in use. For visualising a print on a copper-based object, the amount of $CuBr.S_4N_4$ used is envisaged to be approximately 0.15 grams for a 6.5-litre volume chamber. For visualising a print on a stainless steel-based object, it is envisaged that 0.3 grams of $CuBr.S_4N_4$ can be used for a 6.5-litre volume chamber.

After providing a sealed chamber (5) via operation of moveable arm (8), $CuBr.S_4N_4$ is heated for about 1 minute, under a vacuum of about 13 Pa (0.1 mmHg) obtained via vacuum port (6), at a temperature to about 180° C. obtained via thermal communication with the first heating element (10*a*, 10*b*), to decompose the $CuBr.S_4N_4$ and produce $S_2N_2$ vapour. The $S_2N_2$ enters the sealed chamber (5) and contacts the object comprising a print, while $S_2N_2$ by-products can accumulate on the inner sides of the cartridge as a result of the thermal gradient, and/or the funneling, along the cartridge.

The sealed chamber (5) containing the object comprising a print to be visualised can be then left to develop for about 15 minutes. Fingerprint development is observed as $S_2N_2$ vapour polymerises on the object being treated. During this time, the second heating element (11*a*, 11*b*, 11*c*, 11*d*) is heated at about 50° C. to preventing crystallisation of $S_2N_2$ on the surface of the base (2) of the apparatus (1).

Upon completing the duration in which the $S_2N_2$ vapour contacts the object (2), the vacuum is removed from sealed chamber (5) via vacuum port (6) and, after releasing the housing (4) via moveable arm (8), the $S_2N_2$ vapour is removed via the fume hood.

Various modifications to the apparatus (1) can be made as will be apparent to those skilled in the art. For example, the size of the housing (2) can be varied in size and/or shape according to the desired application. For example, the housing can provide for a sealed chamber with a volume of 13 litres (i.e. having dimensions of approximately 201 millimetres in diameter by 400 millimetres in height, so therefore taller in orientation than the embodiment described for FIGS. 1-2). In this instance, it is envisaged that approximately 0.3 grams of $CuBr.S_4N_4$ can be used for visualising a print on a copper-based object, while 0.6 grams of $CuBr.S_4N_4$ can be used for visualising a print on a stainless steel-based object. A fan, such as a stirring fan, may be provided to assist with the dispersion of $S_2N_2$ vapour when the apparatus is used to implement the method of the invention for visualising a print on an object. The housing (4) may be rectangular or square in shape. The apparatus may also not require use of a cartridge, but the receptacle could be adapted to receive the agent and to provide the thermal gradient when heated, and/or the funneling, such as the upper portion of the receptacle could extend beyond the heater pot (7*a*), and could for example comprise, or consist essentially, of a poor conductor of heat or an insulator, such as glass. Furthermore, a receptacle and/or cartridge of different size and/or shape may be envisaged, for example wherein in use, a different portion of the cartridge can protrude from the receptacle, in order to optimise the thermal gradient and/or the funneling.

It will be understood that the present invention has been described above purely by way of example, and modification of detail can be made within the scope of the invention. Each feature disclosed in the description, and (where appropriate) the claims and drawings may be provided independently or in any appropriate combination.

Moreover, the invention has been described with specific reference to fingerprint visualisation. It will be understood that this is not intended to be limiting and the invention may be used more generally. For example, the invention may be used more generally in the forensic fields, and may be used in other chemical applications. Additional applications of the invention will occur to the skilled person.

The invention claimed is:
1. An apparatus for visualizing a print on an object, the apparatus comprising:
   a base defining a surface, the base comprising a first heating element in thermal communication with a receptacle having an opening adapted to receive an agent, the receptacle protruding from the surface of the base;

a housing adapted to contact the base to provide a sealed chamber; and a port adapted to apply a vacuum to or release a vacuum from the sealed chamber, wherein the receptacle comprises, along its length, two portions: a first portion, at the base of the receptacle, in contact with, or designed to be heated directly by, the first heating element; and a second portion, adjacent to the opening to the receptacle, either not in contact with, or not directly heated by, the first heating element, wherein the first portion of the receptacle comprises a heat conductive material, and the second portion of the receptacle comprises a material that is (i) less heat conductive than the heat conductive material of the first portion or (ii) an insulating material.

2. An apparatus according to claim 1 wherein the receptacle is arranged such that the first heating element is capable of generating a thermal gradient in the receptacle.

3. An apparatus according to claim 1 wherein the housing is connected to the apparatus by a moveable arm.

4. An apparatus according to claim 1 wherein the first heating element and receptacle are arranged substantially centrally on the base.

5. An apparatus according to claim 1 wherein the base comprises a second heating element in thermal communication with the surface of the base.

6. An apparatus according to claim 1 wherein the apparatus comprises a control interface.

7. An apparatus according to claim 1 wherein the heat conductive material of the first portion of the receptacle comprises metal and the material of the second portion of the receptacle comprises glass.

8. An apparatus according to claim 1 wherein each of the first portion and the second portion comprises a height and wherein the height of the second portion is one of approximately half, twice or three times the height of the first portion.

9. An apparatus according to claim 8 wherein the height of the second portion is approximately 1.5 times the height of the first portion.

10. A system for visualizing a print on an object, the system comprising:

the apparatus of claim 1;

a cartridge designed to be, or suitable for being, inserted into the receptacle of the apparatus of claim 1; and an amount of agent within the cartridge, wherein the agent is a metal halide of $S_4N_4$.

11. A system according to claim 10 wherein the cartridge comprises a sealable means designed to be removed prior to use.

12. A system according to claim 11 wherein the agent is pre-weighed and provided in the sealed cartridge.

13. A system according to claim 7 wherein the agent is $CuBr.S_4N_4$.

14. A method for visualizing a print on an object using the system of claim 7, the method comprising the steps of:

a) placing the cartridge containing the agent in the receptacle;

b) arranging the object on or proximal to the base;

c) placing the housing on the surface of the base to form a sealed chamber enclosing the object, cartridge and agent;

d) removing air from the sealed chamber via the port to provide a vacuum;

e) heating the agent in the cartridge via the first heating element to generate vapour within the sealed chamber;

f) allowing the vapour to contact the object;

g) releasing the vacuum via the port;

h) removing the housing to allow for off-gassing; and i) removing the object for inspection and/or downstream image recording.

15. A method according to claim 14 wherein the agent is $CuBr.S_4N_4$.

16. A method for visualizing a print on an object using the apparatus of claim 1, the method comprising the steps of:

a) placing the agent in the receptacle;

b) arranging the object on or proximal to the base;

c) placing the housing on the surface of the base to form a sealed chamber enclosing object and agent;

d) removing air from the sealed chamber via the port to provide a vacuum;

e) heating the agent in the receptacle via the first heating element to generate vapour within the sealed chamber;

f) allowing the vapour to contact the object;

g) releasing the vacuum via the port;

h) removing the housing to allow for off-gassing; and i) removing the object for inspection and/or downstream image recording.

17. A method according to claim 11 wherein the agent is a metal halide of $S_4N_4$.

18. A method according to claim 12 wherein the agent is $CuBr.S_4N_4$.

19. A method according to claim 11 wherein the vacuum is at a pressure of from about $1.33 \times 10^{-6}$ Pa to about 133 Pa.

20. A method according to claim 16 wherein for step e) the agent is heated at a temperature of from about 160° C. to 200° C. for at least 30 seconds.

21. A method according to claim 16, wherein a second heating element heats the surface of the base for a period of time during at least one of steps d) to h) and/or prior to step d).

22. A method according to claim 21 wherein the second heating element is heated at a temperature of from about 25° C. to 160° C.

23. A method according to claim 16 wherein the apparatus is operated within a fume hood.

24. A method according to claim 16 wherein at least one of steps c) to e) and steps g) to h) is controlled by a control interface.

25. Use of the apparatus of claim 1, to visualize a print on an object.

* * * * *

UNITED STATES PATENT AND TRADEMARK OFFICE
CERTIFICATE OF CORRECTION

PATENT NO. : 11,937,919 B2
APPLICATION NO. : 17/250818
DATED : March 26, 2024
INVENTOR(S) : Roberto Stefano Pasquale King, Martin Wayne Millington and Andrew Worsfold Page 1 of 1

It is certified that error appears in the above-identified patent and that said Letters Patent is hereby corrected as shown below:

In the Claims

Column 13, Line 57, Claim 13, replace "A system according to claim 7 wherein the agent is" with -- A system according to claim 10 wherein the agent is --.

Column 14, Line 2, Claim 14, replace "system of claim 7, the method comprising the steps of:" with -- system of claim 10, the method comprising the steps of: --.

Column 14, Line 24, Claim 16, replace "a sealed chamber enclosing object and agent" with -- a sealed chamber enclosing the object and agent --.

Column 14, Line 34, Claim 17, replace "A method according to claim 11 wherein the agent is" with -- A method according to claim 16 wherein the agent is --.

Column 14, Line 36, Claim 18, replace "A method according to claim 12 wherein the agent is" with -- A method according to claim 17 wherein the agent is --.

Column 14, Line 38, Claim 19, replace "A method according to claim 11 wherein the vacuum" with -- A method according to claim 16 wherein the vacuum --.

Signed and Sealed this
Seventeenth Day of September, 2024

Katherine Kelly Vidal
*Director of the United States Patent and Trademark Office*